(12) United States Patent
Gagliano

(10) Patent No.: US 10,463,459 B2
(45) Date of Patent: Nov. 5, 2019

(54) POWER VARYING PEDAL

(71) Applicant: Steven Gagliano, Kings Park, NY (US)

(72) Inventor: Steven Gagliano, Kings Park, NY (US)

( * ) Notice: Subject to any disclaimer, the term of this patent is extended or adjusted under 35 U.S.C. 154(b) by 48 days.

(21) Appl. No.: 15/923,454

(22) Filed: Mar. 16, 2018

(65) Prior Publication Data
US 2018/0200035 A1 Jul. 19, 2018

Related U.S. Application Data

(63) Continuation of application No. 14/451,078, filed on Aug. 4, 2014, now Pat. No. 9,931,185, which is a continuation of application No. 12/986,633, filed on Jan. 7, 2011, now abandoned.

(60) Provisional application No. 61/356,721, filed on Jun. 21, 2010.

(51) Int. Cl.
| A61C 1/00 | (2006.01) |
| A61C 17/20 | (2006.01) |
| G10H 1/34 | (2006.01) |
| A61M 37/00 | (2006.01) |
| H02J 4/00 | (2006.01) |

(52) U.S. Cl.
CPC .......... *A61C 17/20* (2013.01); *A61M 37/0084* (2013.01); *G10H 1/348* (2013.01); *H02J 4/00* (2013.01)

(58) Field of Classification Search
CPC .......... A61C 1/0023; A61C 17/20; H02J 4/00; A61M 37/0084; G10H 1/348
USPC ................... 433/101; 74/512–514; 200/86.5; 251/295; 318/551; 606/186
See application file for complete search history.

(56) References Cited

U.S. PATENT DOCUMENTS

| | | | | |
|---|---|---|---|---|
| 3,989,952 A | * | 11/1976 | Hohmann | A61C 1/0015 307/38 |
| 4,479,182 A | * | 10/1984 | Beier | A61C 1/0023 433/101 |
| 4,639,710 A | * | 1/1987 | McMillan | H01C 10/106 200/86.5 |
| 5,382,891 A | * | 1/1995 | Huffener | G10H 1/0008 318/269 |
| 5,535,642 A | * | 7/1996 | Moll | H01H 3/14 200/86.5 |
| 6,893,261 B1 | * | 5/2005 | Feine | A61C 1/0023 433/101 |
| 7,012,203 B2 | * | 3/2006 | Hanson | A61B 17/00 200/86.5 |
| 2007/0122096 A1 | * | 5/2007 | Temelkuran | A61B 18/201 385/126 |
| 2008/0166685 A1 | * | 7/2008 | Rosenblood | A61C 1/0015 433/101 |

(Continued)

FOREIGN PATENT DOCUMENTS

JP  2004522503  7/2004

*Primary Examiner* — Matthew M Nelson
(74) *Attorney, Agent, or Firm* — Tutunjian & Bitetto, P.C.

(57) ABSTRACT

A system and method for providing variable power is disclosed. The system includes a power supply which provides power to at least one instrument. A pedal comprises a variable resistor that is configured to produce a resistance value within a predetermined range based on an amount of pressure which is being applied to the pedal. The voltage being supplied to the instrument is varied in accordance with the resistance value produced at the pedal.

9 Claims, 16 Drawing Sheets

(56) References Cited

U.S. PATENT DOCUMENTS

2009/0125050 A1* 5/2009 Dixon ............... A61M 37/0076
                                              606/186
2009/0183602 A1* 7/2009 Crockett ........... A61M 37/0076
                                              81/9.22
2009/0272221 A1* 11/2009 Long ...................... G05G 1/305
                                              74/514

* cited by examiner

POWER VARYING PEDAL

RELATED APPLICATION INFORMATION

This application is a Continuation application of co-pending U.S. patent application Ser. No. 14/451,078, filed on Aug. 4, 2014, which is a continuation of U.S. patent application Ser. No. 12/986,633, filed on Jan. 7, 2011, now abandoned.

BACKGROUND

Technical Field

The present invention relates to supplying varying power levels to an instrument and, more particularly, it relates to a power varying pedal which uses a variable resistor to vary the voltage being supplied to an instrument.

Description of the Related Art

It is often the case that workers, professionals or artists are required to operate a hand-held instrument, tool or other device which can be tuned to a variety of different speeds or power levels. For example, tattoo artists operate a tattoo machine or gun when applying artwork to human skin and may adjust the speed of the needle, dentists operate an ultrasonic dental scaler when cleaning a patient's mouth and may adjust the speed at which the scaler vibrates, construction workers operate a drill for boring and may adjust the speed at which the drill rotates, etc.

In order to adjust the speed of the motor or the power level of these instruments, the operator must typically stop working and manually adjust a knob or dial by hand. The knob or dial may be located on a power source associated with the instrument or on the instrument itself. However, touching of the knob may cause health issues, especially in the case involving dentists and tattoo artists, where bodily fluids, blood, germs, pathogens or contaminants may be transferred from the operator's glove to the tuner or, vice versa, from the tuner to the operator's glove. In addition, such adjustments tend to distract the operators from the task at hand, and in some cases may require the operator to turn off the instrument being used. Even further, if the operator wishes to precisely tune the instrument to a specific power level, manually adjusting a dial by hand tends to be difficult, especially in cases where the operator is wearing gloves. Thus, it would be advantageous to allow these operators to adjust the speed or power level of such instruments without having to stop what they are doing and without having to use their hands.

SUMMARY OF THE INVENTION

In accordance with the present principles, a system for providing variable power is disclosed. The system includes a pedal configured to produce a resistance value within a predetermined range based on an amount of pressure which is being applied to the pedal. The system also includes a means for regulating the voltage being supplied to an instrument in accordance with the resistance value produced at the pedal.

In accordance with the present principles, a method for providing variable power is disclosed. According to the method, a resistance value is produced within a predetermined range based on an amount of pressure that is being applied to the pedal. The voltage being supplied to an instrument is varied in accordance with the resistance value produced at the pedal.

Other objects and features of the present principles will become apparent from the following detailed description considered in conjunction with the accompanying drawings. It is to be understood, however, that the drawings are designed solely for purposes of illustration and not as a definition of the limits of the present principles, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views.

DETAILED DESCRIPTION

Figure 1A:
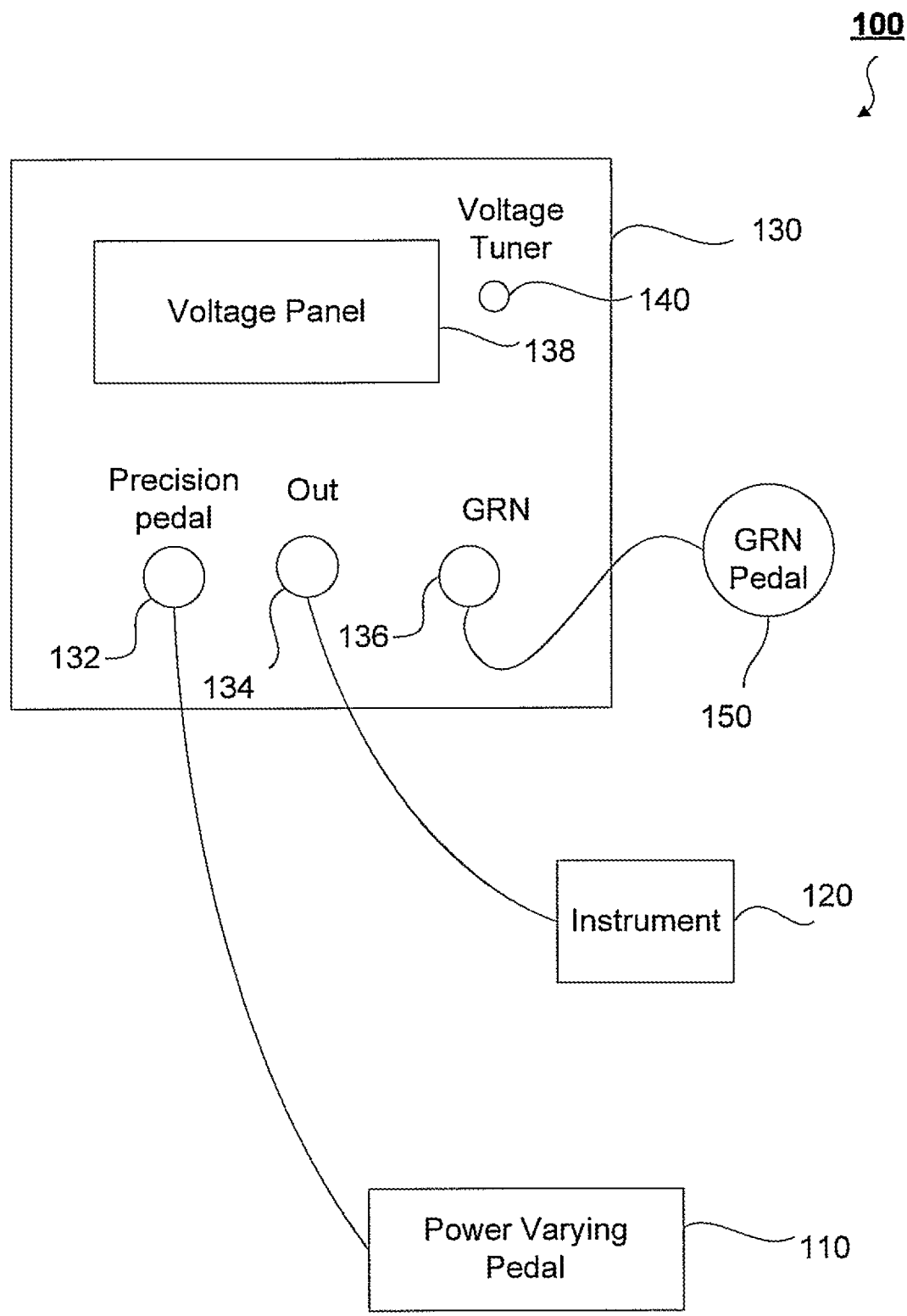
FIG. 1A is a variable power supply system including a variable power source in accordance with one embodiment of the present principles.

In accordance with the present principles, a "power varying pedal" is provided which can adjust the amount of current being provided to an operator's instrument and thereby alter the speed or power level of the instrument (e.g., by altering the speed of the instrument's motor). The power varying pedal may be coupled to a "variable power source" which supplies varying levels of voltage or current to an instrument depending upon how far the power varying pedal is depressed. In another embodiment, the power varying pedal is connected to an external "variable power adapter" which is in turn is connected to a conventional power supply. In this case, the variable power adapter regulates the amount of voltage passing through the adapter to an instrument, and thereby changes the power level of the instrument. In an even further embodiment, a power varying pedal is connected directly to a conventional power source and an instrument, and a variable power adapter incorporated into the power varying pedal permits a varying amount of voltage to be provided to the instrument.

Upon reading this description, it will be apparent to those skilled in the art that the principles described herein have many advantageous uses and can be applied in a wide variety of applications or circumstances. For example, in one particularly useful embodiment, the present principles may be applied to a tattoo application system. Tattoo artists operate a hand-held tattoo machine or tattoo gun to apply ink to human skin. The tattoo machine includes a needle can puncture the skin at varying rates (e.g., 50 to 3,000 per minute). During the process of applying a tattoo to a person, the operator of the tattoo machine is typically required to manually adjust the speed of the needle by hand (e.g., by turning a dial on a conventional power source). However, touching of the knob may transfer blood, germs, pathogens or other contaminants to the tuner, or may transfer the same to the hand of the operator. Moreover, manually adjusting a knob by hand may distract the tattoo artist from his or her work, and further, may be quite difficult if the artist is wearing gloves.

To address these issues, the present principles provide a tattoo artist with a power varying pedal which allows the artist to vary the amount of voltage being supplied to the tattoo machine by depressing the pedal (e.g., by stepping on the pedal with his or her foot). Since the artist is not required to turn a knob or tuner by hand, the artist can avoid the risk of passing blood-borne pathogens or other infectious agents. In addition to providing safer operating conditions the pedal power varying pedal gives the artist greater control over the tattoo machine than had been permitted by conventional systems, thus allowing him to apply artwork to the human skin in an easier and more precise manner. Other advantages stem from the fact that the pedal described herein allows the artist to change the speed of the needle without having to stop work and without having to use his or her hands.

In another useful embodiment, the present principles can be applied to an ultrasonic dental scaler used by a dentist. Ultrasonic dental scalers are hand-held instruments which use high-frequency vibrations to remove deposits from the surface of a patient's tooth. Traditionally, the dentist must remove the instrument from the patient's mouth and turn a dial on the instrument to adjust the frequency of the vibrations. However, the power varying pedal according to the present principles permits the dentist to change the frequency of the vibrations while the dentist continues to work on the patient and without having to remove the instrument from the patient's mouth. And once again, it prevents the dentist from spreading germs, bodily fluids or other infectious agents since the dentist can change the power level of the scaler without using his hands.

Although the above two examples of the present principles involve tattoo equipment and dentistry equipment, one skilled in the art would recognize that the present principles are applicable to numerous types of different devices, and especially to devices which allow for varying voltage or varying power levels. For example, the present principles may be applied to a construction drill for boring holes which is capable of operating at differing power levels. Therefore, it should be recognized that the exemplary uses of the teachings described herein are not limiting, and that the examples discussed herein are for pedagogical purposes to aid the reader in understanding the present principles.

Referring now to the drawings in which like numerals represent the same or similar elements and initially to FIG. 1, a variable power supply system 100 is illustratively depicted in accordance with one embodiment of the present principles. The system includes a power varying pedal 110, an instrument 120, a variable power source 130 and a GRN pedal 150 (optional). The variable power source includes a voltage tuner 140 and a voltage panel 138. In addition, the variable power source disclosed in this particular embodiment includes three connections: a power varying pedal connection 132, an out connection 134 for outputting voltage or current to a device or instrument 120, and a GRN pedal connection 136.

Instrument 120 may be a device which can be operated at varying power levels or varying speeds. In one particularly useful embodiment, instrument 120 comprises a tattoo machine which includes a needle and a motor capable of operating at different speeds to vary the rate at which the needle moves. In another embodiment, instrument 120 comprises an ultrasonic dental scaler which can operate at different power levels to vary the rate at which the instrument vibrates. It should be noted that instrument 120 can comprise a variety of other devices as well (e.g., a drill used to bore holes).

Instrument 120 is connected to a variable power source 130 which can provide differing levels of voltage to the instrument 120, thus changing the speed or power level of the instrument 120. The variable power source 130 receives input from the power varying pedal 110 regarding the amount of voltage that is to be supplied to the instrument 120 and outputs voltage to instrument 120 in accordance with the input. In one embodiment, variable power source 130 is a 120 VAC transformer which provides consistent direct current (DC) power that can be adjusted by the power varying pedal 110.

The power varying pedal 110 is powered by the variable power source 130 and comprises a variable resistor (e.g., rheostat or potentiometer). The variable resistor produces a resistance value within a predetermined range when the pedal is depressed. The resistance value is used by the variable power source 130 to adjust the amount of current or voltage that is being supplied to the instrument 120 by the variable power source 130. Varying the voltage may cause a motor at the instrument to operate at different speeds. In the embodiment where instrument 120 comprises a tattoo machine, this will cause a variation in the speed at which the needle moves. In the embodiment where instrument 120 comprises a dental scaler, this will cause a variation in the rate at which the device vibrates.

A tattoo artist, dentist or other operator can step on the pedal 110, or apply pressure to the pedal 110 in other ways, to vary the voltage being supplied to the instrument 120. The amount of voltage being supplied to the instrument 120 will vary within a certain range depending upon how far the pedal is depressed. In one embodiment, the amount of voltage being supplied to instrument 120 will increase as the power varying pedal 110 is depressed further and further. Thus, fully depressing the pedal 110 will result in the greatest amount of voltage being supplied to the instrument 120. On the other hand, failing to depress the pedal 110 in any manner whatsoever may result in no voltage being supplied to the instrument 120, or alternatively, may result in a predetermined minimal level of voltage being supplied to the instrument 120. It should be recognized that the power varying pedal 110 can be configured in a number of other ways to vary the voltage being supplied to the instrument 120.

In one embodiment, the amount of voltage being supplied to instrument 120 is directly proportional to the percentage at which the power varying pedal 110 is depressed. For example, suppose variable power source 130 is capable of varying the voltage being supplied to instrument 120 between 0-10V direct current (DC) power. In this case, depressing the pedal 120 down sixty percent of the pedal range would thus supply 6V DC power to instrument 120.

In another embodiment, a number of different predetermined threshold values are used to operate the instrument 120 at a number of predetermined speeds or power levels. Using the tattoo machine example, the machine may be configured to vary the movement of the needle at three predefined speeds depending up how far the pedal 110 has been depressed. For example, the tattoo machine would operate at a first speed if the pedal 110 is depressed 0%-33%, a second speed if the pedal 110 is depressed 34%-66%, and a third speed if the pedal is depressed 67%-100%. One of ordinary skill in the art would recognize that various other methods may be applied to vary the voltage which is being supplied to instrument 120.

While the power varying pedal 110 allows an operator to adjust the voltage being supplied to an attached instrument 120, the voltage tuner 140 provides an alternate mechanism for adjusting the voltage being supplied to the instrument 120. Voltage tuner 140 allows an operator to manually adjust the voltage being supplied to the tattoo machine 120 by turning a dial or knob. However, in addition to spreading infectious agents, this manner of adjusting the voltage may distract an operator from the task at hand and tends to be cumbersome if the operator is wearing gloves. Regardless of whether the voltage tuner 140 or the power varying pedal 110 is used to adjust the voltage, voltage panel 138 displays the level of voltage which is being supplied to instrument 120.

The variable power source 130 and/or instrument 120 can alternatively be turned on in the traditional sense by depressing GRN pedal 150 if present. For example, disconnecting power varying pedal 110 and connecting GRN pedal 150 and subsequently stepping on GRN pedal 150 will power up instrument 120. Stepping on GRN pedal 150 will provide full power to the instrument 120 in the traditional use of this device. It should be noted that other ways of turning on/off the power supply 130 or instrument 120 may be employed (e.g., flipping a switch or pressing a button which is located on the power source).

The three connections on variable power source 130 (i.e., the power varying pedal connection 132, the out connection 134 and the GRN pedal connection 136) represent sockets, jacks (e.g., RTS jacks) or other interfaces which can receive a plug (e.g., mono plugs) or other connecting pieces. Specifically, connection 132 provides an interface for connecting the power varying pedal 110 to the variable power source 130. Similarly, the out connection 134 provides an interface for connecting an instrument 120 and for supplying variable voltage to the instrument 120, and the GRN pedal connection 136 provides an interface for connecting the GRN pedal 150 to the power supply 130.

Figure 1B:
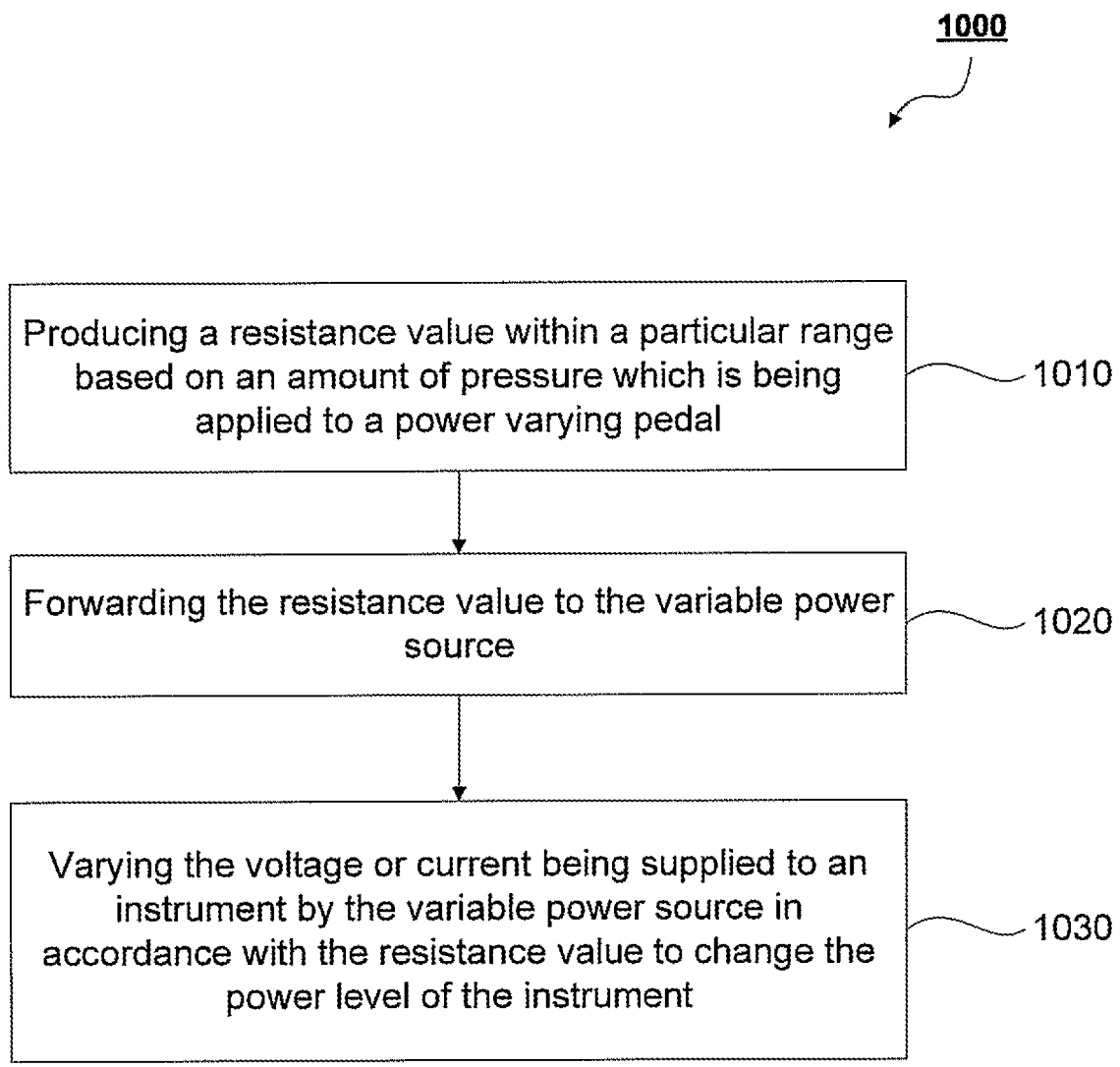
FIG. 1B is a block/flow diagram illustrating an exemplary method for providing a variable power supply using the variable power source disclosed in FIG. 1A.

Referring now to FIG. 1B, a block/diagram discloses a method 1000 for providing a variable power supply system 100 using the variable power source 130 depicted in FIG. 1A. In step 1010, a power varying pedal 110 produces a resistance value using a variable resistor, such as a rheostat or potentiometer. The resistance value reflects the amount of pressure which is being applied to the power varying pedal 110 (e.g., by stepping on the pedal). The resistance value information is forwarded to a variable power source 130 (step 1020). This may involve sending the resistance value over a wire which is connected to both the variable power pedal 110 and the variable power source 130 using mono plugs. However, it should be noted that the present principles may involve transmitting this value to the variable power source using other means (e.g., fiber optic connections, wireless connections, etc.).

In step 1030, the resistance value information is used at the variable power source 130 to adjust the amount of voltage or current which is being supplied to an instrument 120. This will cause a change in the power level at which the instrument is operating (e.g., by changing the speed of the instrument's motor). Varying the voltage level may involve using the resistance value produced by pedal 120 to set or adjust the amount of voltage that is being resisted at the variable power source 130.

Figure 2A:
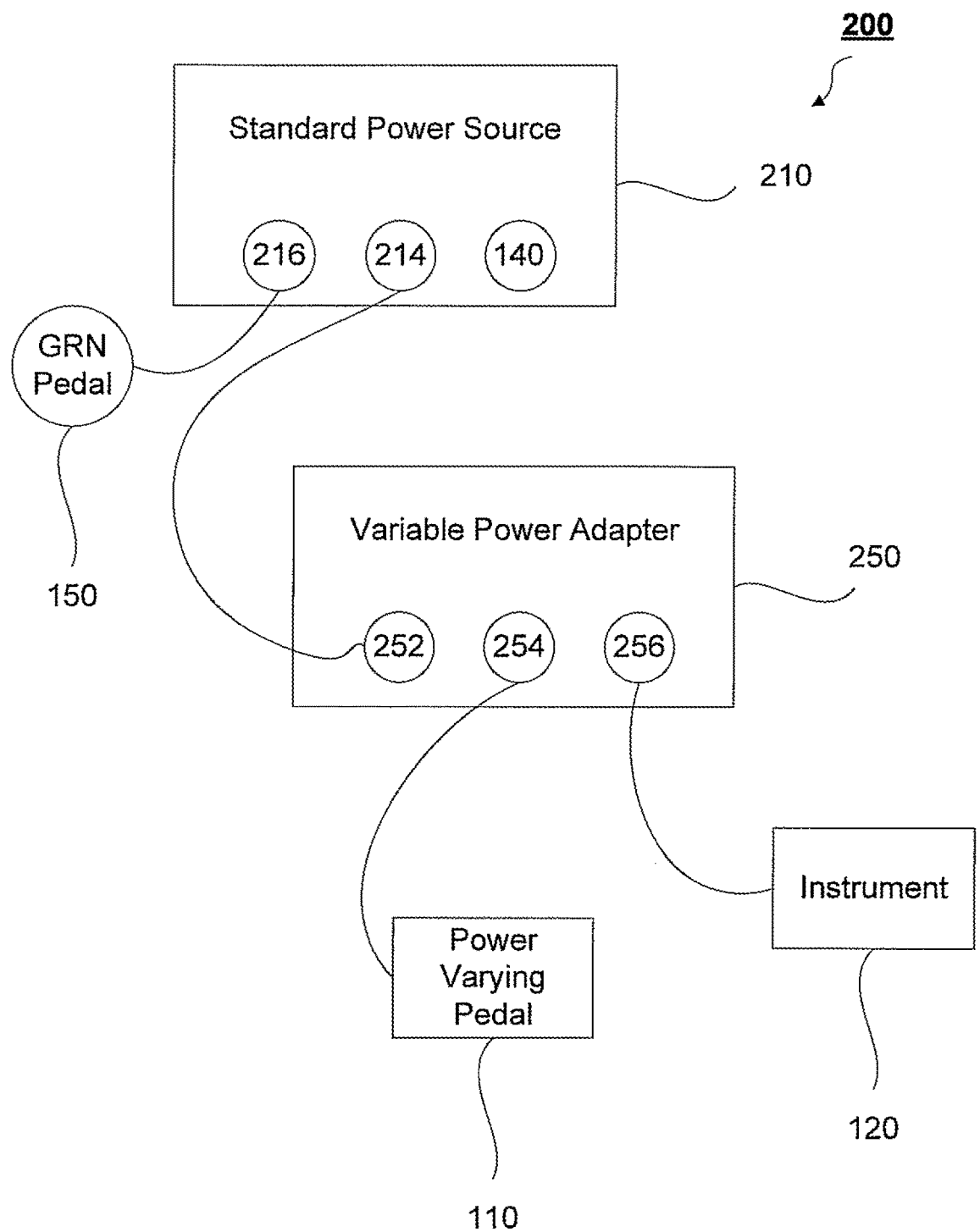
FIG. 2A is a variable power supply system including a variable power adapter which regulates the current being supplied to an instrument from a conventional power source in accordance with another embodiment of the present principles.

Moving on to FIG. 2A, an alternate variable power supply system 200 is disclosed which permits variable voltage or variable current to be supplied to an instrument 120 from a standard power source 210. The system comprises a standard power source 210, a variable power adapter 250, a GRN pedal 150 and a power varying pedal 110.

Standard power source 210 relates to a conventional power source which is only capable of varying the current or voltage being supplied to instrument 120 by turning voltage tuner 140 by hand. Unlike the variable power source 130 described above, standard power source 210 does not include an interface for receiving input from a power varying pedal 110 and has no means to use such input to vary the voltage being output. Standard power source 210 includes two connection interfaces: a GRN pedal connection 216 for connecting GRN pedal 150 and an "out" connection 214 which outputs voltage.

The variable power adapter 250 allows for the voltage which is being supplied to instrument 120 by the standard power source 210 to be adjusted within a certain range depending upon how far power varying pedal 110 has been depressed. The variable power adapter 250 receives a current from the standard power source 210 and regulates the manner in which the current is distributed to the instrument 120 in accordance with resistance value produced by the power varying pedal 110. In doing such, this piece of equipment allows for standard power supplies and standard instrument devices (e.g., standard tattoo machines) to work in conjunction with the power varying pedal 110. In one embodiment, the variable power adapter takes in 24V up to 3 AMP VDC power from the standard power source 210 and allows for variable voltage regulation from 0V to 12V and 1 AMP VDC power out.

Figure 2B:
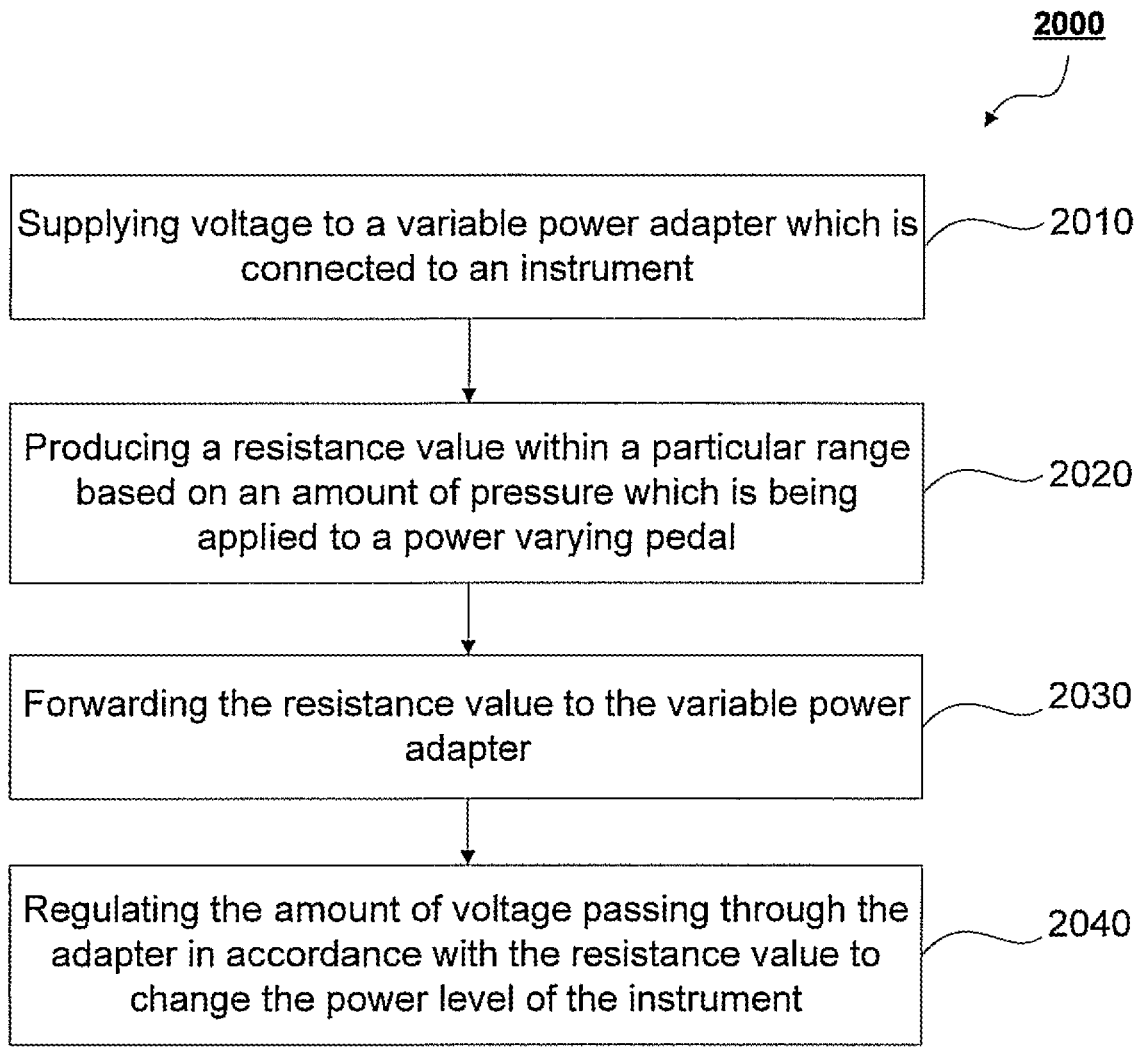
FIG. 2B is a block/flow diagram illustrating an exemplary method for providing a variable power supply using the variable power adapter disclosed in FIG. 2A.

Referring now to FIG. 2B, a block/flow diagram illustratively depicts a method 2000 for providing a variable power supply system 200 using a standard power source 210 in conjunction with a variable power adapter 250 as depicted in FIG. 2A. In step 2010, a conventional power source 210 supplies voltage to a variable power adapter 250, for example, via a cable or wire which connects output connection 214 of the power source 210 and input connection 252 of a variable power adapter 250. Power varying pedal 110 uses a variable resistor to produce a resistance value based on the amount of pressure which is being applied to the power varying pedal (step 2020). The manner in which this value is produced may vary. For example, as explained above, the value produced may be directly proportional to the level at which the pedal is depressed or may involve using predetermined threshold values.

Next, in block 2030, the value is forwarded from the power varying pedal 110 to the variable power adapter 250, possibly via a cable which connects the power varying pedal 110 to connection 254 of the variable power adapter 250. The value is then used in block 2040 by the variable power adapter 250 to regulate the amount of voltage passing through the adapter to the instrument 120, and to thereby change the power level of the instrument 120 connected to the variable power adapter 250. Varying the voltage flowing through the adapter may involve using the resistance value to set or adjust the level of resistance at variable power adapter 250. By adjusting the level of resistance of the variable power adapter 250. the amount of voltage being supplied to the instrument 120 can be altered, thus allowing the instrument 120 to operate at different power levels or at different speeds.

Figure 3A:
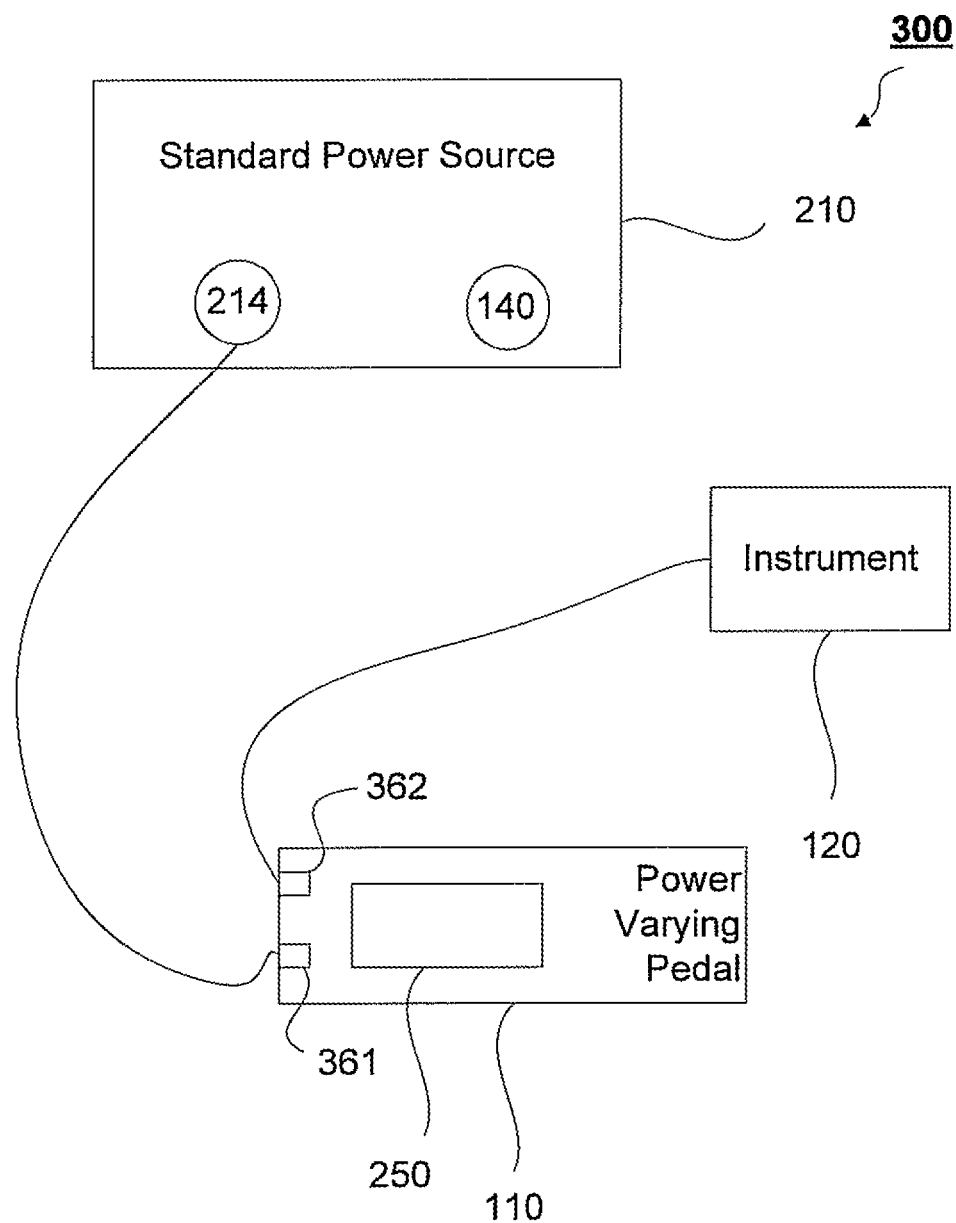
FIG. 3A is a variable power supply system which incorporates a variable power adapter into a power varying pedal to regulate the current being supplied to an instrument from a conventional power source.

FIG. 3A discloses another embodiment of a variable power supply system 300 which regulates the current being supplied to an instrument from a standard power source 210. While the power varying pedals 110 in FIGS. 2A and 3A are both compatible with a standard power supply 210, the embodiment in FIG. 3A does not include a separate variable power adapter 250 component. Rather, in FIG. 3A, the variable power adapter 250 has essentially been incorporated into the power varying pedal 110 to control the level of voltage being supplied to instrument 120. The variable power adapter 250 component incorporated into this embodiment of the power vary pedal 110 performs the same functions as the variable power adapter 250 discussed above in substantially the same manner. Specifically, the variable power adapter component 250 uses a resistance value generated by a variable resistor at the power varying pedal 110 to regulate the amount of voltage passing through the power varying pedal 110 to the instrument 120.

Power varying pedal 110 comprises two connection interfaces: pedal input connection 361 and pedal output connection 362. Standard power source 210 supplies voltage to the power varying pedal 110 via power output connection 214 and pedal input connection 361. Upon connecting power varying pedal 110 to standard power source 210, the power varying pedal 110 and instrument 120 may automatically be turned on.

Power varying pedal 110 is connected to instrument 120 via pedal output connection 362 and provides a varying amount of voltage to the instrument 120 depending upon how far power the power varying pedal 110 is depressed. More specifically, power varying pedal 110 uses a variable resistor to produce a resistance value based on the amount of pressure which is being applied to the power varying pedal 110 in the same manner described above. This value is then used by the variable power adapter component 250 in the power varying pedal 110 to regulate the amount of voltage passing through the pedal to the instrument 120, and to thereby change the power level of the instrument 120.

Figure 3B:
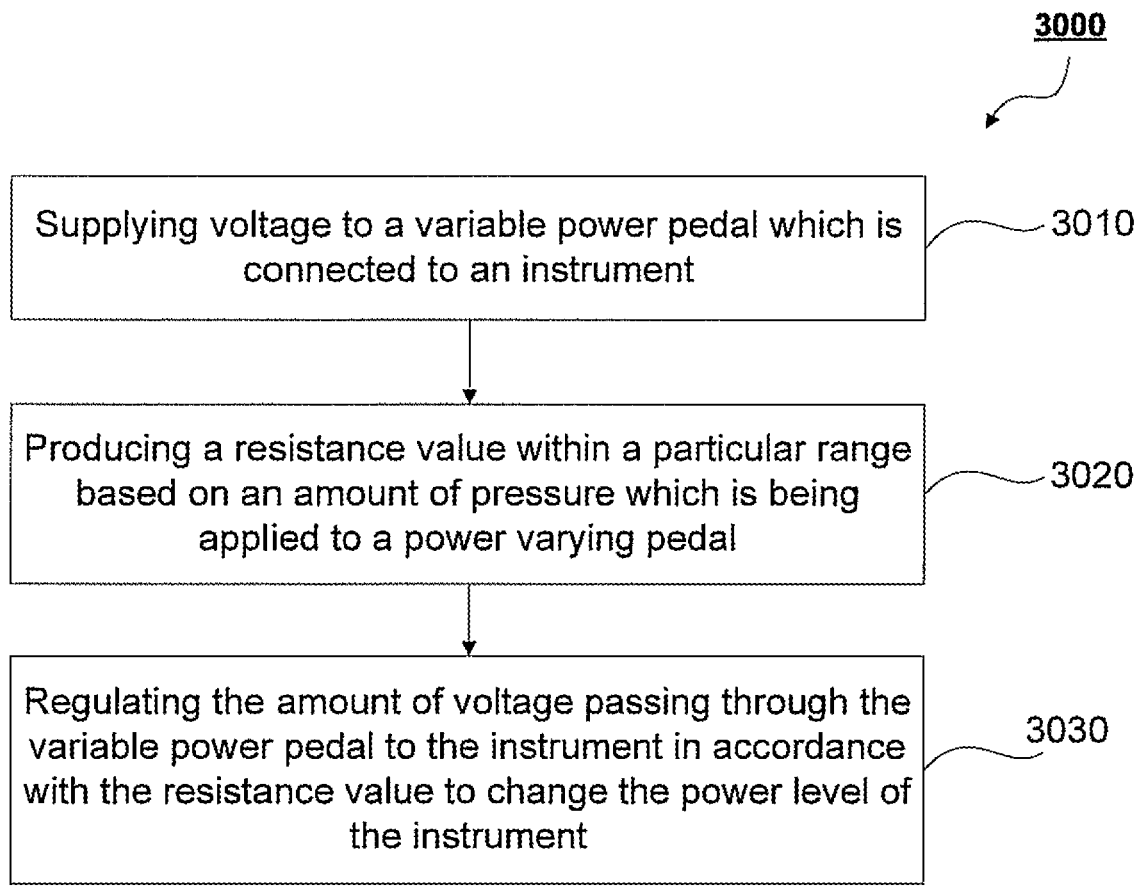
FIG. 3B is a block/flow diagram illustrating a method for providing a variable power supply system using a power varying pedal which incorporates a variable power adapter as disclosed in FIG. 3A.

FIG. 3B is a block/flow diagram illustrating a method 3000 for providing a variable power supply system using a power varying pedal 110 which incorporates a variable power adapter 250. The method begins in step 3010 where voltage is supplied to a power varying pedal 110 which comprises a variable power adapter 250. The power varying pedal 110 is connected to and supplies power to instrument 120.

A variable resistor (e.g., potentiometer or rheostat) in the power varying pedal 120 produces a resistance value within a particular range based on the amount of pressure which is being applied to the power varying pedal 110 (step 3020). The amount of voltage being supplied to the instrument 120 connected to the power varying pedal 110 is varied based on the amount of pressure being applied to the power varying pedal 110 (step 3030). More specifically, the voltage passing through power varying pedal 110 to the instrument 120 depends on the resistance value which is produced by the variable resistor. As explained above, varying the voltage level may involve using the resistance value produced by pedal 120 to set or adjust the amount of voltage that is being resisted at the variable power source 130.

One of ordinary skill in the art would recognize that the various embodiments disclosed above could be altered in a variety of different ways. For example, rather than employing the variable power adapter 250 as a separate component (as in FIG. 2A) or incorporating the variable power adapter 250 into the power varying pedal 110 (as in FIG. 3A), the variable power adapter 250 could be incorporated into the instrument 120. In this embodiment, the resistance value produced by the power varying pedal 110 could be forwarded to the instrument 120 to adjust the power level of the instrument 120. Many other variations are also contemplated and fall within the scope of the present principles.

Figure 4:
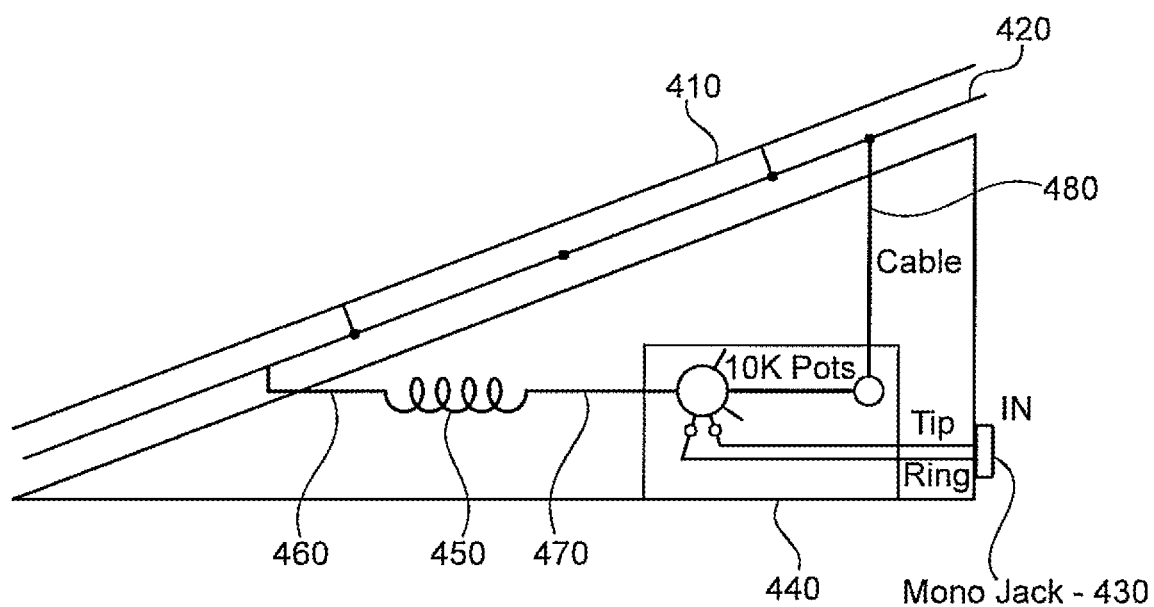
FIG. 4 is an exemplary design for a power varying pedal in accordance with one embodiment of the present principles.

Referring now to FIG. 4, an exemplary power varying pedal 110 is illustratively depicted in accordance with one embodiment of the present principles. The particular pedal disclosed in this figure may be used with the variable power supply system disclosed in FIGS. 1A and 2A.

As can be seen, the power varying pedal 110 has a pedal surface 410 which can be depressed (e.g., by stepping on it) to adjust the voltage being supplied to an instrument 120. The pedal surface 410 is connected to a pedal anchor 420 which in turn is connected to two different cables or wires 460, 480 as illustrated in the figure. Tension spring 450 is attached to cable 460 and cable 470. Cables 470 and 480 are coupled to a 10K potentiometer (10K POTS) 440 which in turn is connected to mono jack 430. The "ring" and the "tip" notations used in this figure refer connections from the mono jack.

The 10K potentiometer 440 produces a resistance value based on how far pedal surface 410 has been depressed. A variable power source 130 or a variable power adapter 250 attached to the power varying pedal 110 may use this value to adjust the amount of voltage which is being resisted. The 10K potentiometer 440 is turned via a cable system (e.g., involving cables 460, 470 and 480) which turns the 10K potentiometer knob. As the pedal is depressed forward, the cable turns the POTS knob 440 and the voltage is varied up. As the pedal is depressed back, the POTS knob 440 and the voltage is varied down.

More specifically, depressing the pedal surface 410 will cause the pedal anchor 420 to pull on the cables 460, 470, 480 and the tension spring 450 to produce a resistance value at the POTS 440. This resistance value may be outputted to either a variable power source 130 or a variable power adapter 250 via a mono jack connection. The resistance value is then used by the variable power source 130 or a variable power adapter 250 to adjust the amount of current or voltage that is being supplied to an instrument 120.

An alternate embodiment of a power varying pedal 110 is illustratively depicted in FIGS. 5A-5D. The particular embodiment disclosed in this figure may be used with the power varying system disclosed in FIG. 3A.

The power varying pedal 110 includes two connections, e.g., which may receive mono plugs or other connecting pieces. Connection 361 provides a connection between the pedal 110 and a conventional power source 210, while connection 362 provides a connection between the pedal 110 and the instrument 120. The pedal also includes a detent assy 510 comprising a spring-loaded ball 521 (or equivalent mechanism), and a series of gears 521, 522A, 522B, 523A, 523B, 524A and 524B.

Figure 5A:
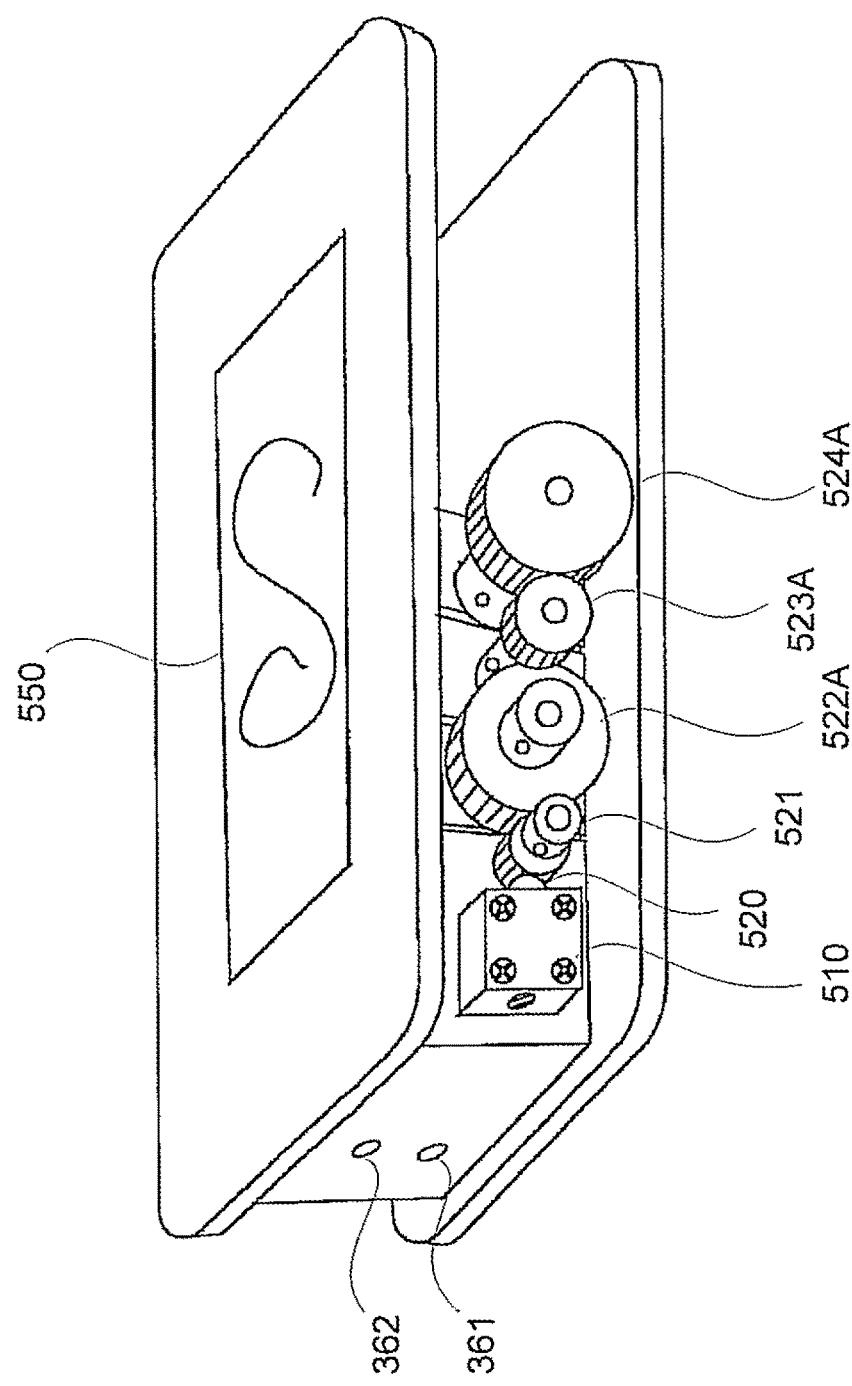
FIG. 5A is an exemplary design for a power varying pedal in accordance with another embodiment of the present principles.

Unlike the embodiment shown in FIG. 4, the embodiment in FIG. 5A does not employ a series of cables in conjunction with a tension spring to adjust the resistance value produced by the variable resistor in the pedal 110. Rather, the power varying pedal 110 employs a series of gears in conjunction with the detent assy 510 to adjust the resistance value produced by the variable resistor in the pedal 110. The resistance value produced in this manner is then used at the pedal to vary the voltage which is being supplied to a connected instrument 120.

Figure 5B:
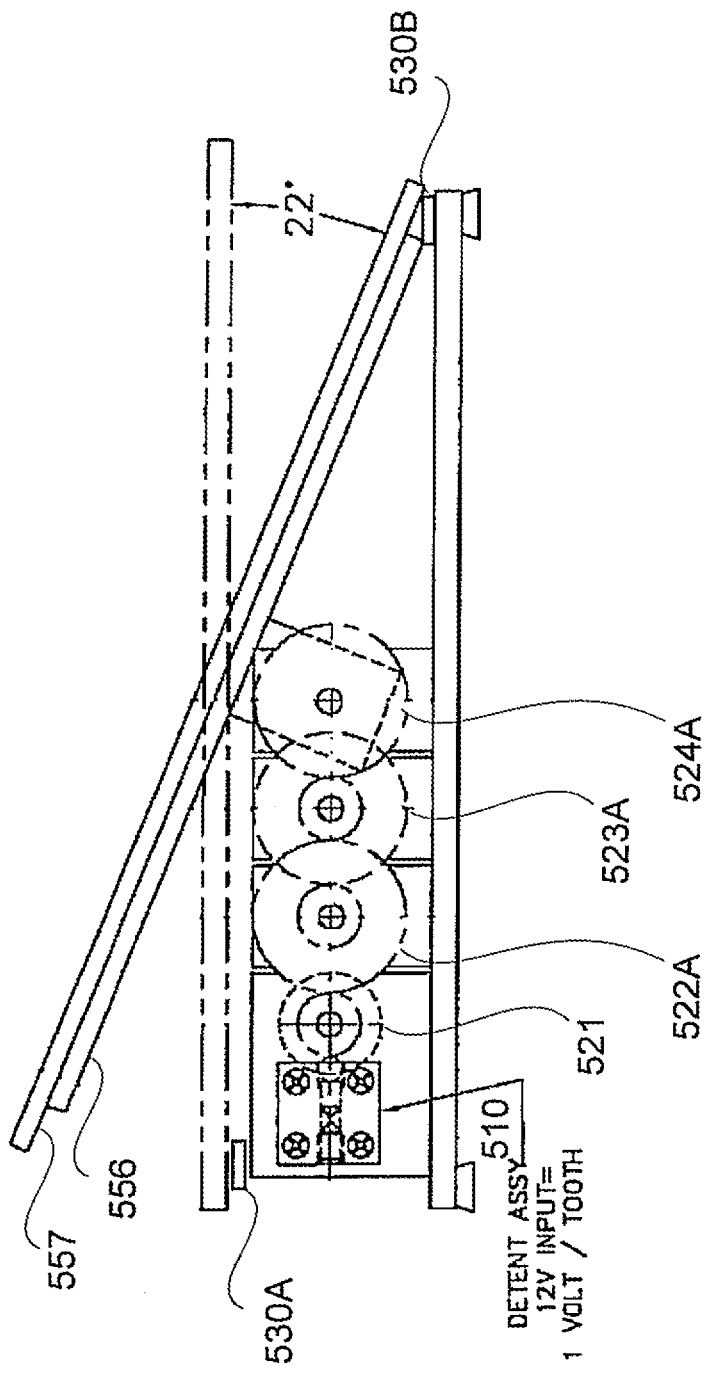
FIG. 5B is a more detailed side view of the power varying pedal illustrated in FIG. 5A.
Figure 5C:
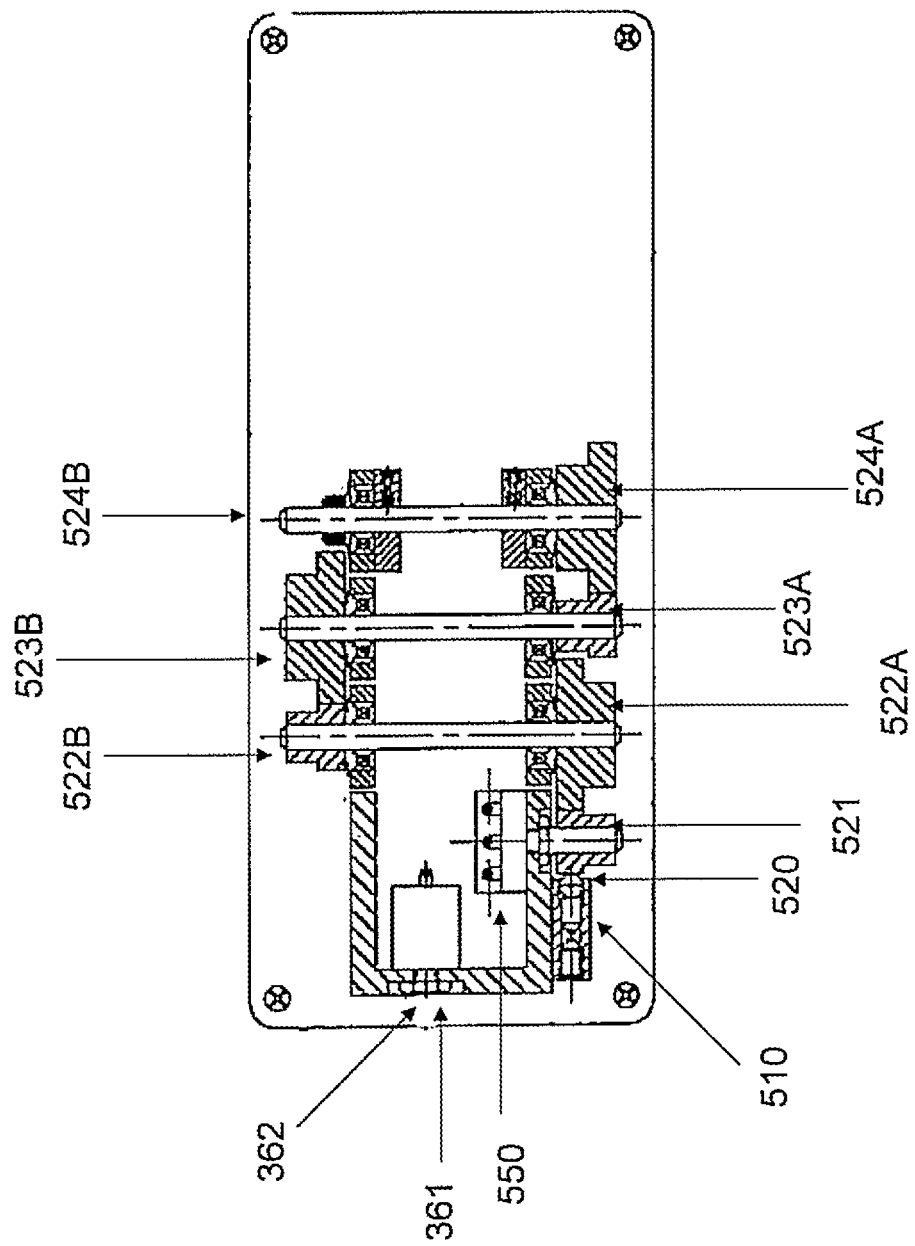
FIG. 5C is a top view disclosing the internal configuration of the power varying pedal in FIG. 5A.

Although gears can be arranged in a number of different configurations, the zigzag ratio of the gearing illustrated in FIG. 5C may be preferred for a number of reasons. Specifically, the particular configuration of gears provides an arrangement where the potentiometer is turned one click at a base of 1V for a 12V inputted power. This permits precise control over the amount of power which is being supplied to the instrument 120. In addition, the particular configuration of the gears results in a pedal which is more durable, and which is esthetically appealing.

In certain embodiments, the pedal is configured in a manner which allows an operator to leave the pedal in a specific position while taking his or her foot of the pedal. Hence, the instrument can be operated without the operator's foot on the pedal, and the operator would only need to step on the pedal to adjust the current which is being supplied to the instrument. As a result, the operator is provided with more mobility.

When the pedal 110 is depressed, the gears 524A and 524B will begin to rotate. The rotation of gears 524A and 524B cause the other gears to rotate. Specifically, gear 524A is interlocked with gear 523A, thus causing gears 523A and 523B to rotate. Gear 523B is interlocked with gear 522B, thus causing gears 522B and 522A to rotate. Similarly, gear 522A is interlocked with gear 521, thus causing gear 521 to rotate.

The detent assy 510 includes a spring-loaded ball 520 which fits into a notch on gear 521. The detent assy is also connected to a variable resistor 550 (e.g., a potentiometer) as illustrated in FIG. 5B. Each time gear 521 rotates a predetermined distance, the spring-loaded ball 520 is received by the next notch on gear 521. As the pedal is depressed further and further, the spring-loaded ball 520 is continuously fitted into each adjacent notch on gear 521. For each notch on gear 521, the resistance value produced by the variable resistor 550 is adjusted a predetermined amount, thus causing the voltage being supplied to the instrument 120 to be increased a predetermined amount. Stopping blocks 530A and 530B ensure that the voltage being supplied to the instrument 120 is supplied within a pre-determined range.

As an operator takes his or her foot off of the pedal 110, or applies less pressure to the pedal 110, the gears rotate in the opposite direction and the spring-loaded ball 520 moves to each adjacent notch in gear 521 in the opposite direction than it had taken when the pedal was being depressed. As gear 521 rotates in the opposite direction, the resistance value produced by the variable resistor 550 is adjusted a predetermined amount, thus causing the voltage being supplied to the instrument 120 to be decreased a predetermined amount.

The above manner of operating the power varying pedal in FIGS. 5A-D is now illustrated by way of example. Suppose that the power varying pedal 110 is configured to provide varying voltage to an instrument 120 within the range of 1-12V. As the pedal is depressed, the gears 521-524 will rotate in a first direction (e.g., clockwise). As gear 521 rotates, the spring-loaded ball 520 is received by consecutive notches on gear 521. Each time the spring-loaded ball 520 is received by a different notch, the variable resistor 550 adjusts the resistance value such that the voltage output by the varying power pedal 110 to the instrument 120 increases by 1V. More specifically, each time the spring-loaded ball 520 moves to the next notch in gear 521, a resistance value is produced by the variable resistor 550 which is then utilized by the variable power adapter 250 component incorporated into the pedal to increase the voltage being output by 1V.

The stopping blocks 530A and 530B ensure that the power varying pedal 110 outputs voltage within the predetermined range of 1-12V. As illustrated in FIG. 5B, these stopping blocks ensure that the total variation between the initial position of the pedal and the final position of the pedal (when the pedal is fully depressed) is within a range of 22 degrees.

Staying with the above example, the pedal operates in a similar manner as an operator applies less and less pressure to the pedal, or takes his foot of the pedal. As less pressure is applied, the gears, including gear 521, rotate in the opposite direction than when the pedal 110 was being depressed (e.g., counterclockwise). Each time the spring-loaded ball 520 moves to the next notch in gear 521, a resistance value is produced by the variable resistor 550. The resistance value is then used by the variable power adapter 250 to decrease the voltage being output by 1V.

Figure 5D:
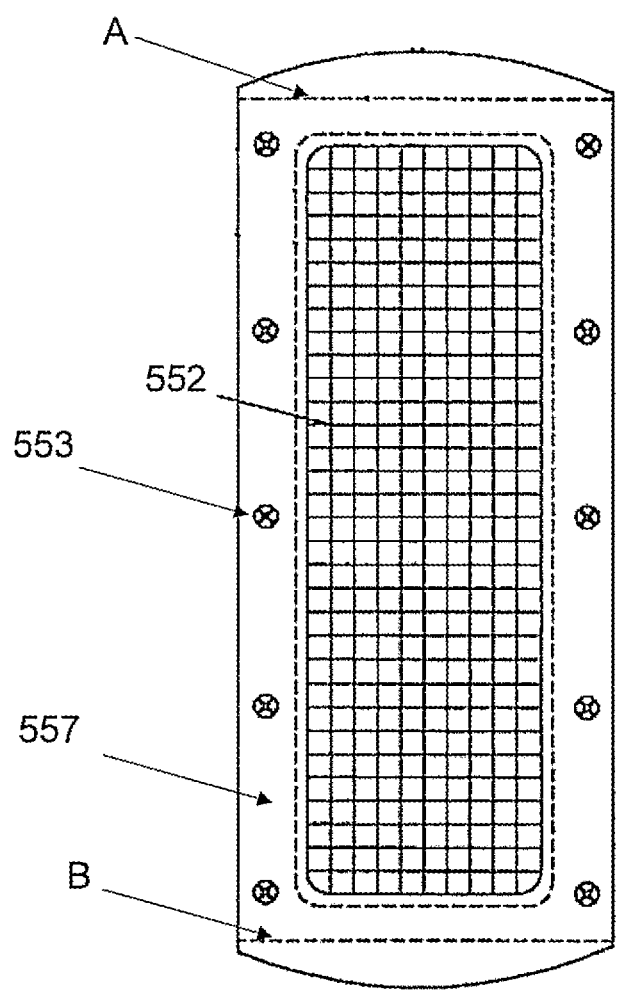
FIG. 5D is a top view disclosing an exemplary external configuration of the power varying pedal in FIG. 5A.

An advantageous configuration for the surface of a pedal is illustratively depicted in FIG. 5D. When viewed from a side perspective (e.g., as in FIG. 5B), the surface of the pedal is primarily comprised of bottom pedal surface 556 and a top pedal surface 557. Bottom pedal surface 556 and top pedal surface 557 are attached to each other by some type of connecting mechanism 553, e.g., a series of screws. The dotted lines labeled A and B reflect the outer edges of bottom pedal surface 556 which lies beneath top pedal surface 557.

Upon disconnecting the pedal surfaces, a gripping mechanism 552 may be inserted in between the surfaces. In FIG. 5D, the pedal is outfitted with a gripping mechanism 552 which comprises a metal grate. The metal grate permits an operator to securely grip the pedal his or her foot, and provides the operator with greater control over the instrument 120. Although the gripping mechanism 552 depicted comprises a metal grate, it should be recognized that numerous other gripping mechanisms may be employed.

Figure 5E:
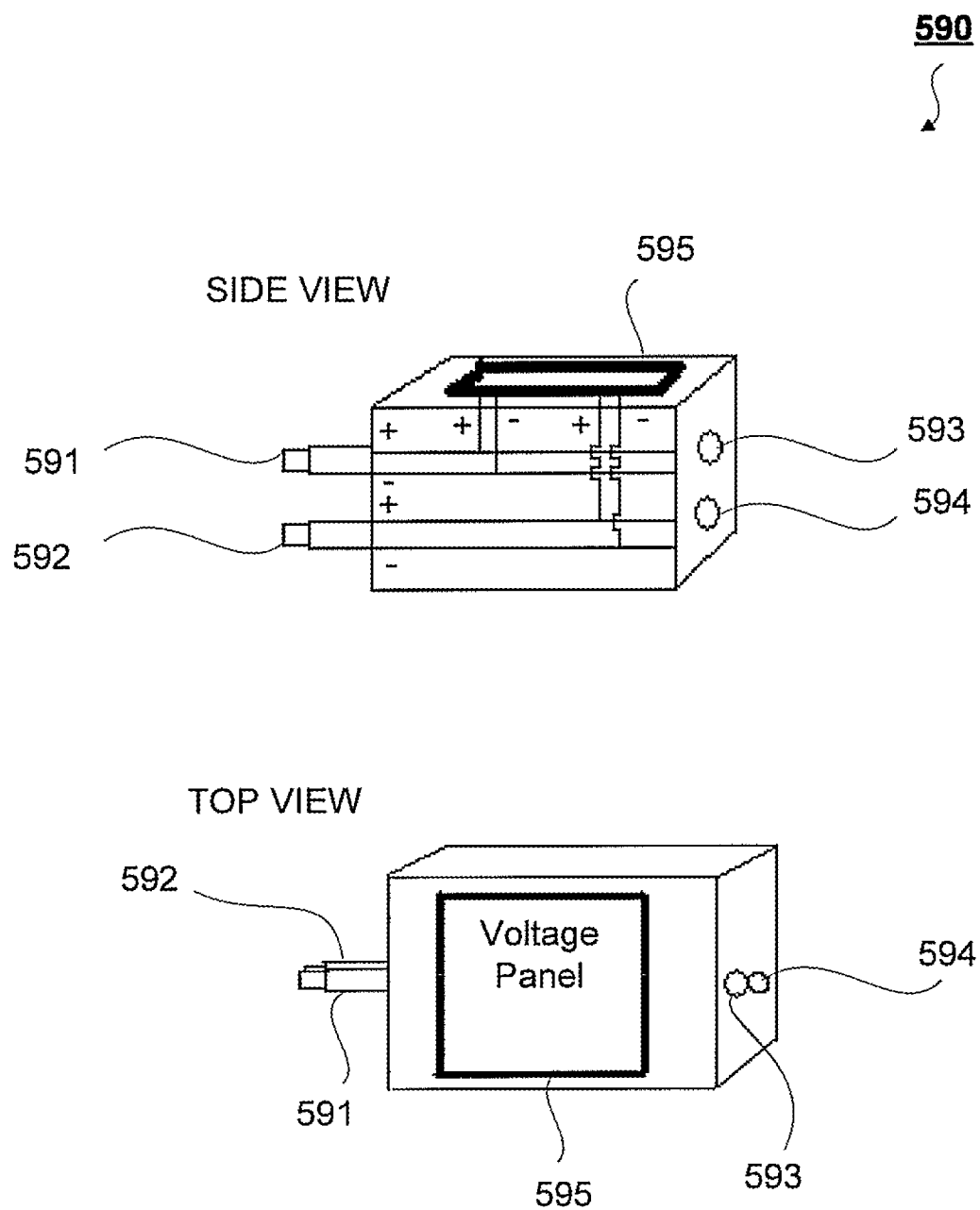
FIG. 5E is an exemplary voltage meter attachment piece for use with the power varying pedal in FIG. 5A.

Moving on to FIG. 5E, an exemplary voltage meter attachment piece 590 for use with the power varying pedal in FIG. 5A is illustratively depicted. The voltage meter attachment piece 590 serves an intermediary piece which is connected directly to the power varying pedal 110, and to both the instrument 120 and the standard power source 210. Voltage passages from a standard power source 210 through the voltage meter attachment piece 590 to the power varying pedal 110. After the power varying pedal 110 adjusts the level of voltage being output to a connected instrument 120 in the manner described above, the voltage display panel 595 located on the voltage meter attachment piece 590 displays the level of voltage output from the power varying pedal 110.

It should be recognized that the standard power source 210 and the instrument 120 are not directly connected to the power varying pedal 110 (e.g., as shown in FIG. 3A). Rather, the standard power source 210 and the instrument 120 are connected to the voltage meter attachment piece 590 which, in turn, is connected to the power varying pedal 110. More specifically, the voltage meter attachment piece 590 includes two connecting pieces, connector 591 and connector 592, which connect the voltage meter attachment piece 590 to the power varying pedal 110 (e.g., via connections 361 and 362 on the power varying pedal 110). Connectors 591 and 592 may comprise mono plug connectors or other known connecting mechanisms. The voltage meter attachment piece 590 also includes connections 593 and 594 for receiving connecting pieces associated with the standard power source 210 and the instrument 120, respectively.

When voltage is supplied from a power source, the voltage passes through connection 593 and output via connector 591. Connector 591 is plugged into connection 361 on the pedal 110, and thus relays the voltage to the power varying pedal 110. The power varying pedal 110 adjusts the level of voltage depending upon how far the pedal 110 is depressed. The voltage output from the power varying pedal 110 is output via connection 362 to connector 592. The voltage meter attachment piece 590 measures the amount of voltage being output from the power varying pedal 110 and outputs this on voltage display 595. The voltage is then output from the voltage meter attachment piece 590 to the instrument 120 via connection 594.

In light of the above description of the varying power pedals 110, one of ordinary skill in the art would recognize that many alterations could be made to these pedals within the scope of the present principles. For example, a number of factors could be varied including, but not limited to, the number of gears and/or cables utilized by the pedals, the range of voltage supplied by the pedals, the range of the pedal's starting and ending positions, the number of stopping blocks, the pedal surface, etc.

Figure 6A:
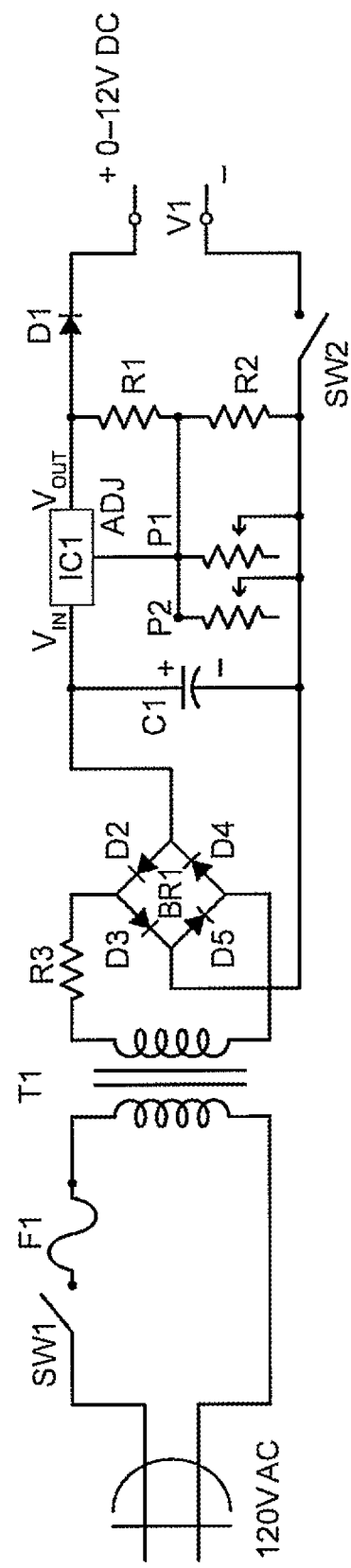
FIG. 6A is a circuit schematic for a variable power source in accordance with one embodiment of the present principles.
Figure 6B:
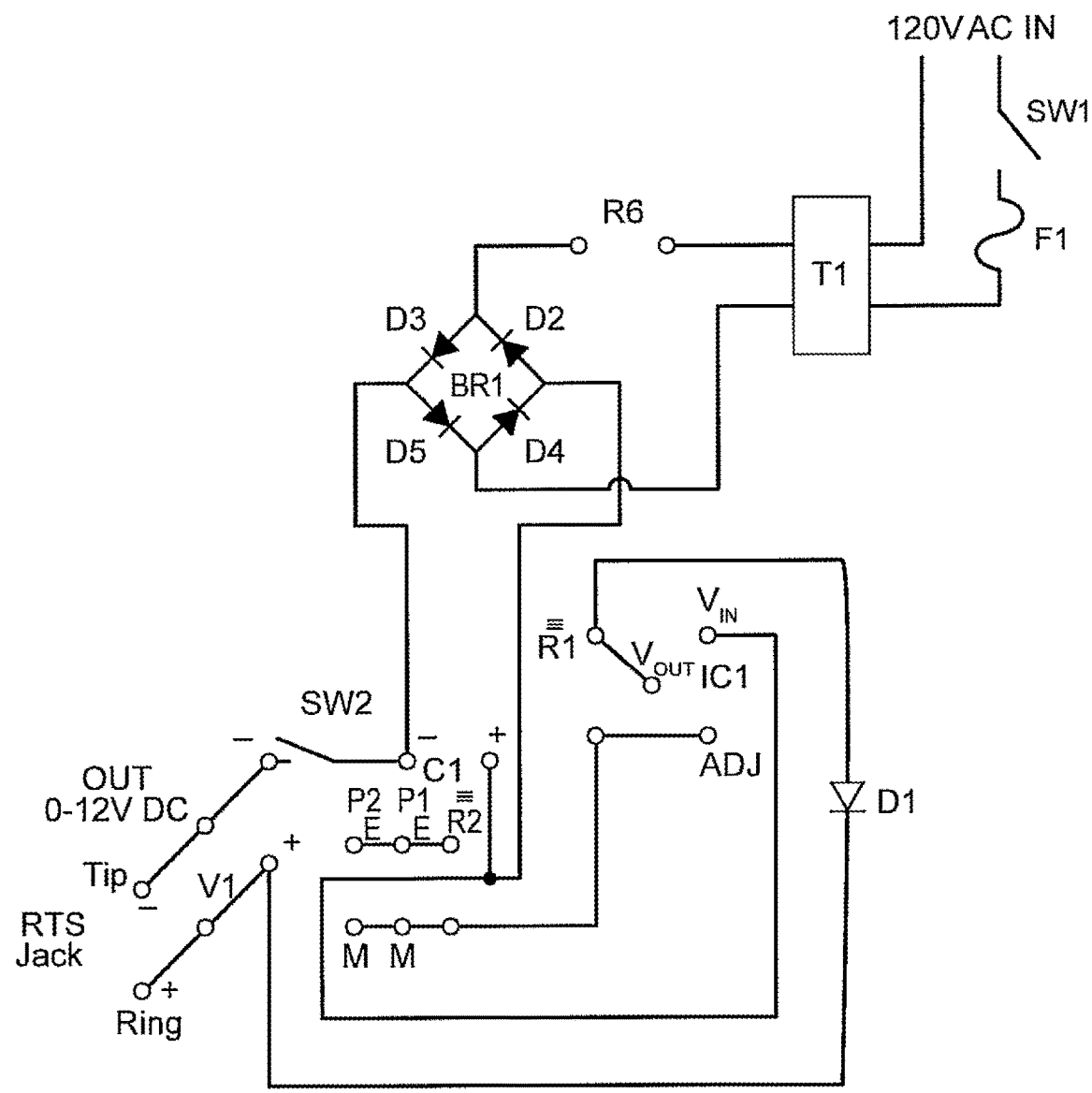
FIG. 6B is a printed circuit board layout for a variable power source in accordance with one embodiment of the present principles.
Figure 7A:
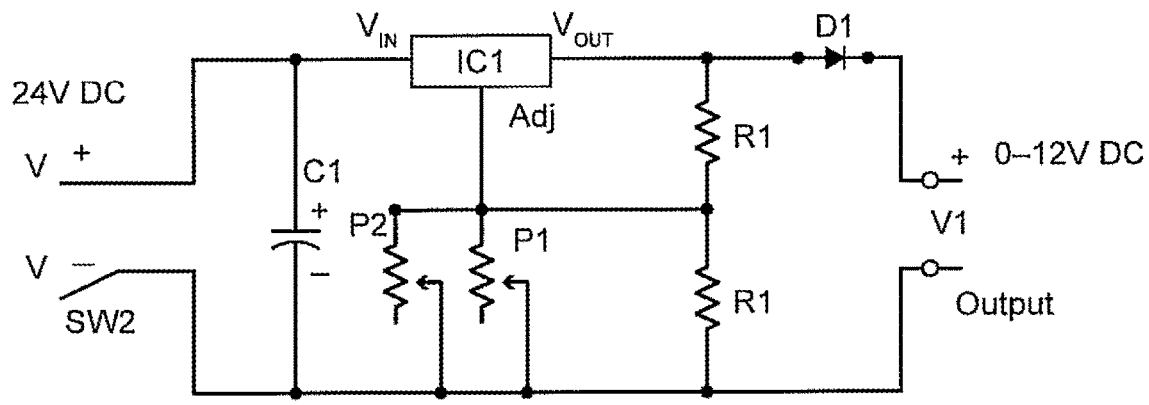
FIG. 7A is a circuit schematic for a variable power adapter in accordance with one embodiment of the present principles.
Figure 7B:
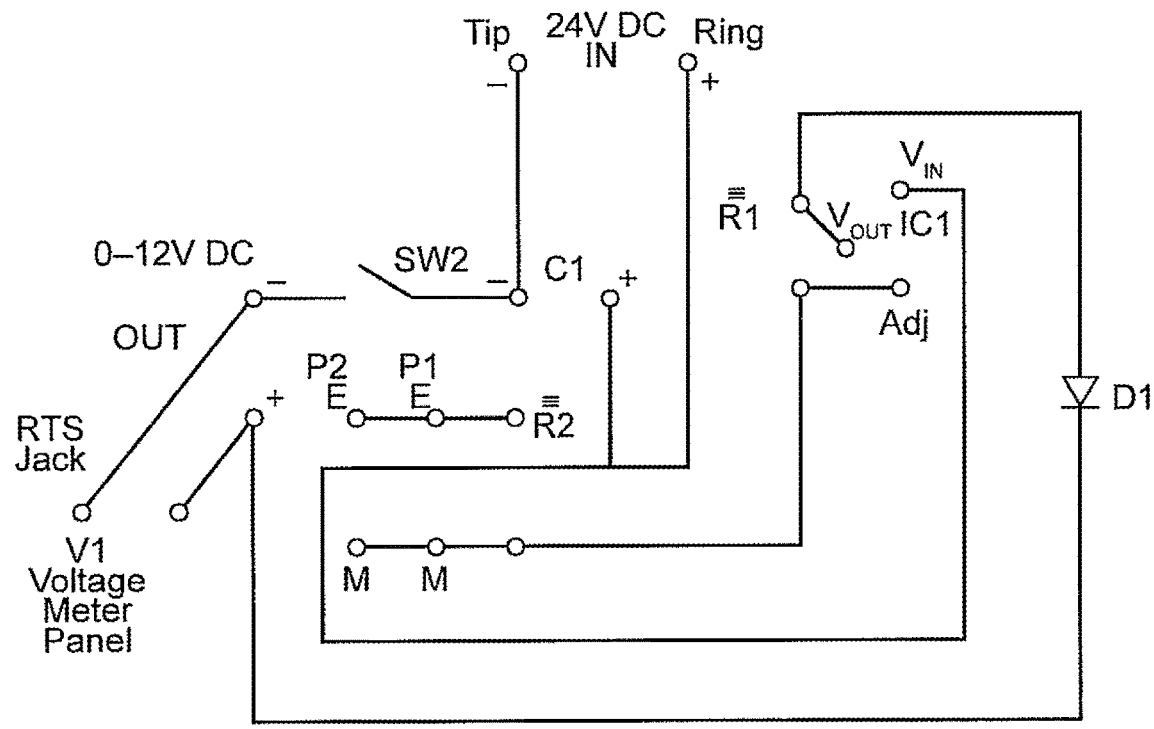
FIG. 7B is a printed circuit board layout for a variable power adapter in accordance with one embodiment of the present principles.
Figure 8:
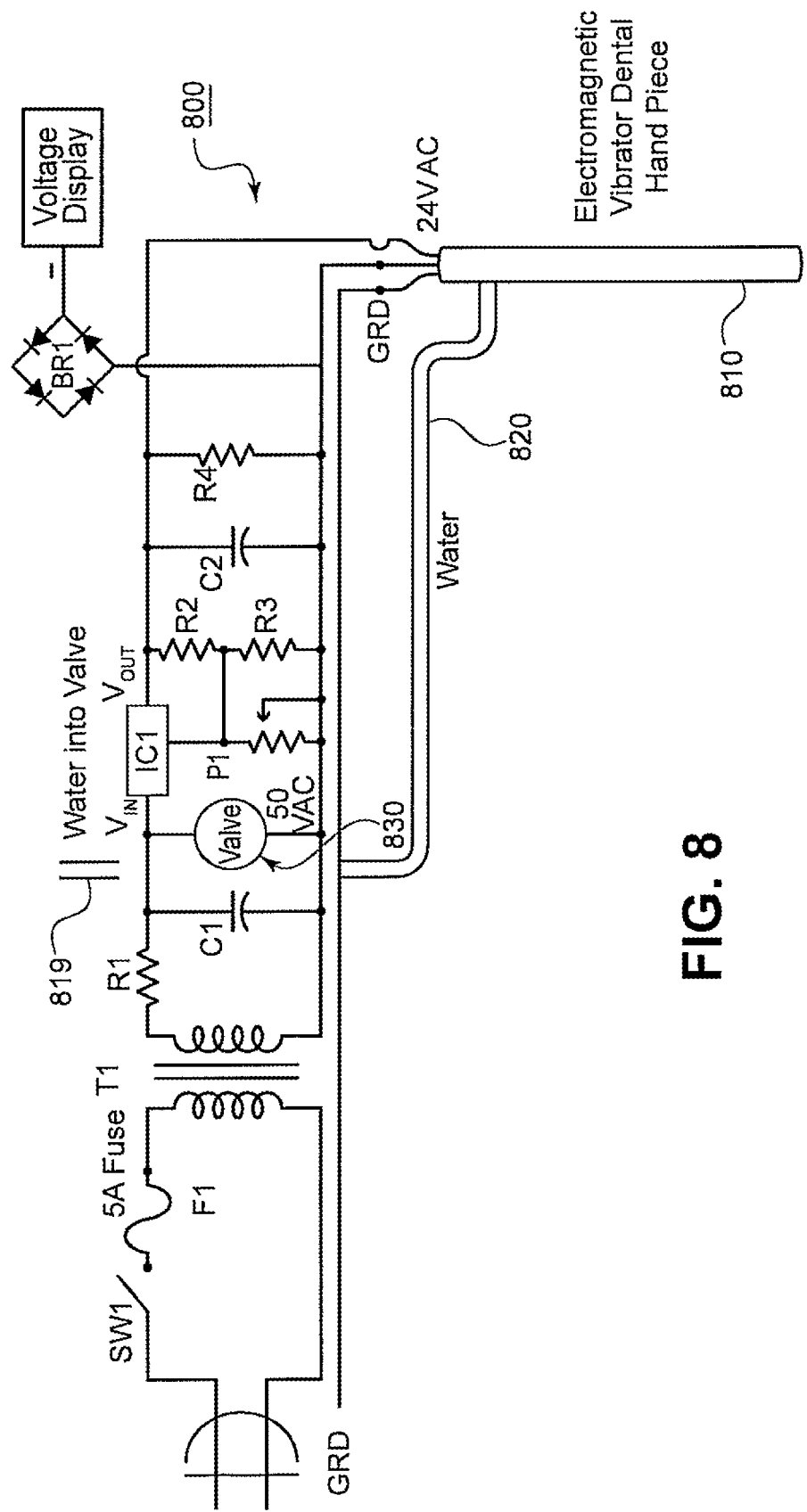
FIG. 8 is a circuit schematic for a variable power ultrasonic dental scaler in accordance with one embodiment of the present principles.

FIGS. 6A, 6B, 7A, 7B and 8 disclose exemplary circuit schematics and printed circuit board layouts for use with the present principles. More specifically, FIGS. 6A and 6B illustrate an exemplary circuit schematic and an exemplary printed circuit board (PCB) layout for a variable power source 130 (e.g., as depicted in FIG. 1A). FIGS. 7A and 7B illustrate an exemplary circuit schematic and PCB layout for a variable power adapter (e.g., as depicted in FIG. 2A). FIG. 8 illustrates an exemplary circuit schematic for use with a dental scaler.

Referring to FIGS. 6A and 6B, an exemplary circuit schematic and printed circuit board (PCB) layout is provided for a variable power source 130 in accordance with one embodiment of the present principles. As can be seen in both the circuit schematic and PCB layout, the variable power source 130 depicted in these figures accepts 120V alternating current (AC) power and outputs a current somewhere in the range of 0V to 12V DC power. Table 1 discloses the notations used in these figures.

TABLE 1

| | |
|---|---|
| F1 | Fuse |
| SW1 | 125 V Switch |
| T1 | 24 V 1.5 AMP Transformer |
| R3 | 5.6 Ω Resistor |
| BR1 | Bridge Rectifier (including D2-D5 which each represent –1N 4004 Diode) |
| IC1 | 317 Voltage Regulator |
| C1 | 1000 UF Electrolytic Capacitor |
| P1/P2 | Connection to the 10K Potentiometer |
| R1 | 270 Ω Resistor (Red, Violet, Brown) |
| R2 | 4.7 Ω Resistor (Yellow, Violet, Red) |
| D1 | 1N 4004 Diode |
| V1 | 12 V Voltage Meter Panel |
| SW2 | 12 V Ground Switch |
| P1 | RTS Jack from Power varying pedal |
| P2 | RTS Jack for the GRN Pedal |
| ADJ | Denotes a connection point of the voltage regulation to P1 |
| R6 | 5.6 Ω Resistor |
| Tip | Denotes a connection point for GRN which is part of RTPS Jack |
| Ring | Denotes a connection point for POS which is part of RTS jack |
| E | Used to connect to end post of POTS |
| M | Used to connect to middle post of POTS |

In these figures, a variable power source 130 receives an alternating current of 120V. If the power source 130 is turned on, the switch SW1 will be in a closed position to complete the circuit. Transformer T1 is a 24V 1.5 AMP raises or lowers the power of the received current to ensure that the current is at an appropriate voltage level. The current is then converted from AC power to DC power at bridge rectifier BR1 which includes four-1N 4004 diodes D2-D5. C1 represents a 1000 UF electrolytic capacitor which stores energy and releases it when needed. Voltage regulator or voltage stabilizer IC1 maintains the voltage within required limits despite variations in input voltage.

P1 and P2 are connections to variable resistors (e.g., potentiometer 410 in FIG. 4). More specifically, P1 is the connection to the variable resistor the installed at the power varying pedal (e.g., at 10K POTS in FIGS. 4) and P2 is the connection to the variable resistor associated with the voltage tuner 140. The input received at P1 and P2 is used to vary the amount of voltage that is being resisted. The amount of voltage being output by variable power source 130 is within the range of 0-12V DC power. The level of voltage being output may be displayed by a voltage panel 138 connected at V1.

Referring now to FIGS. 7A and 7B, a circuit schematic and a printed circuit board layout for a variable power adapter 250 is illustratively depicted. The notations used in FIGS. 7A and 7B refer to the same or similar elements in FIGS. 6A and 6B (as set forth above in Table 1). Variable power adapter 250 receives 24V DC power from a standard power source 210 and outputs a current which varies between 0-12V DC power. Voltage regulator or voltage stabilizer IC1 ensures that the voltage level falls within required limits despite variations in input voltage. P1 and P2 once again represent connections to resistors which permit the amount of voltage being output by variable power adapter 250 to be varied within the range of 0-12V DC power in accordance with the input provided by the power varying pedal 110 or the voltage tuner 140. P1 and P2 are utilized in substantially the same manner as described above. The level of voltage being output may be displayed by a voltage panel 138 connected to V1.

Referring now to FIG. 8, a circuit schematic 800 for a variable power ultrasonic dental scaler is illustratively depicted in accordance with one embodiment of the present principles. The notations referred to in Table 1 relate to the same elements in FIG. 8 with the exception of the notations disclosed in Table 2 below.

TABLE 2

| | |
|---|---|
| T1 | 50 V 5 A Transformer |
| F1 | 5 A Fuse Slow Burn |
| C1/C2 | 4700 Ω 50 V Capacitors |
| IC1 | L7815 Positive Voltage Regulator |
| BR1 | Bridge Rectifier (including 1N 4004 diodes) |
| GRD | Standard 110 v ground connection |

The circuit receives 110V AC power from a power source. In this embodiment of a variable power ultrasonic dental scaler, the input from the power varying pedal 110 is provided directly to the dental scalar to adjust the voltage of the device, and thereby adjust the vibration of the device. This differs from conventional scalers which instead use a knob located on the scaler to adjust the voltage of the device.

Moreover, it should be noted that the manner in which the power level of the scaler is adjusted differs from the systems described in FIGS. 1A, 2A or 3A. More specifically, in this alternative embodiment, the resistance value produced by the power varying pedal 110 is supplied directly to the scaler, and this information is used by the scaler in adjusting the power level of the scaler. This is different from the embodiments described above where the adjustment of the voltage is provided by a variable power source 130 (as in FIG. 1A), a separate variable power adapter component 250 (as in FIG. 2A) or a variable power adapter 250 incorporated into the varying power pedal 110 (as in FIG. 3A). However, one of ordinary skill in the art would recognize that the systems in FIGS. 1A, 2A and 3A can be modified in a similar manner.

Referring back to FIG. 8, the scaler hand piece 810 is supplied voltage within a range of 0-24V AC power to vary the power level of an electromagnetic vibrator therein. The power of the alternating current received by the scaler is raised or lowered by transformer T1, which relates to a 50V 5 A transformer, to ensure that the current is at an appropriate voltage level. Voltage regulator or voltage stabilizer IC1 relates to a L7815 positive voltage regulator which ensures that the voltage level falls within a particular range despite variations in input voltage.

A power varying pedal 110 is directly connected to the scaler (e.g., via a mono jack) and provides input via connection P1 to control the amount of voltage resistance. In doing such, the present principles allow for a connected varying pedal 110 to increase or decrease the AC voltage supplied to the hand piece 810 of the scaler by depressing the pedal surface 510, thus replacing the conventional scaler voltage tuner which is traditionally located on the hand piece itself.

In this embodiment where instrument 120 represents a dental scaler, the manner in which water is supplied to the instrument must also be accounted for. To this end, it can be seen that water is supplied via water duct 819 to the water valve 830. Water valve 830 is connected to water duct 820, which in turn is connected to hand piece 810. In this embodiment, water valve 830 is operated using 12/60V AC power and has a ¼" port and a 3/32" orifice body with a 100 MOPD (maximum opening pressure difference), as well as a 0.18" check value (CV) body and 0.21" CV stop.

In certain embodiments of the dental scaler, the value produced by the power varying pedal can be used not only to adjust the level of power being supplied to the instrument 120, but also to adjust the flow of water which is being supplied to the instrument. Hence, as the power level of the dental scaler increases, the flow of water through the dental scaler also increases.

While there have been shown, described and pointed out fundamental novel features of the present principles, it will be understood that various omissions, substitutions and changes in the form and details of the methods described and devices illustrated, and in their operation, may be made by those skilled in the art without departing from the spirit of the same. For example, it is expressly intended that all combinations of those elements and/or method steps which perform substantially the same function in substantially the same way to achieve the same results are within the scope of the present principles. Moreover, it should be recognized that structures and/or elements and/or method steps shown and/or described in connection with any disclosed form or implementation of the present principles may be incorporated in any other disclosed, described or suggested form or implementation as a general matter of design choice. It is the intention, therefore, to be limited only as indicated by the scope of the claims appended hereto.

What is claimed is:

1. A system for providing variable power to a tattoo machine, comprising:
    a pedal having a predefined range of motion defined by an initial zero position and extending to an upper end position, the pedal comprising at least one gear, and an indexing system having an indexing object biased against the at least one gear;
    wherein displacement of the pedal within its predefined range of motion rotates the at least one gear which causes displacement of the indexing object from one notch to a next adjacent notch to provide a resistance value within a predetermined range corresponding to the predefined range of motion of the pedal;
    a means for regulating a voltage supplied to a connected tattoo machine in response to the pedal position and the corresponding resistance value, wherein said voltage regulating means is in communication with said at least one gear, and the indexing system is configured to maintain the pedal in a specific position when a user is not interacting with the pedal.

2. The system of claim 1, wherein the means for regulating voltage comprises a variable power source which receives the resistance value produced by the pedal and utilizes the resistance value to vary an amount of voltage which is output from the variable power source to the connected tattoo machine.

3. The system of claim 1, wherein the means for regulating voltage comprises an external variable power adapter situated between the tattoo machine and a power source, and the voltage passing through the external variable power adapter is varied in accordance with the resistance value produced at the pedal.

4. The system of claim 1, wherein the means for regulating voltage comprises an internal variable power adapter located at the pedal, and the voltage passing through the pedal to the tattoo machine is varied in accordance with the resistance value produced at the pedal.

5. The system of claim 1, wherein a plurality of notches are spaced in said at least one gear according to a desired predetermined resistance value corresponding to a predetermined discrete voltage value, wherein said indexing object in conjunction with said plurality of notches prevent variation between discrete voltage values.

6. The system of claim 1, wherein an amount of voltage being supplied to the tattoo machine is directly proportional to an amount of pressure being applied to the pedal.

7. The system of claim 1, wherein the resistance value is produced using a variable resistor located at the pedal, and the variable resistor comprises one of a rheostat or a potentiometer.

8. The system of claim 1, further comprising a voltage meter attachment component configured to display an amount of voltage being output from the pedal to the instrument.

9. A tattooing system for providing variable power to a tattoo application instrument, comprising:
- a tattoo machine having an electrical connection;
- a pedal having a predefined range of motion defined by an initial zero position and extending to an upper end position, the pedal comprising at least one gear, and an indexing system having an indexing object biased against the at least one gear;
- wherein displacement of the pedal within its predefined range of motion rotates the at least one gear which causes displacement of the indexing object from one notch to a next adjacent notch to provide a resistance value within a predetermined range corresponding to the predefined range of motion of the pedal;
- voltage regulating means connected to the tattoo machine and the pedal for regulating a voltage supplied to a tattoo machine in response to the pedal position and the corresponding resistance value, wherein said voltage regulating means is in communication with said at least one gear, and the indexing system is configured to maintain the pedal in a specific position when a user is not interacting with the pedal.

* * * * *